(12) United States Patent
Ishikawa et al.

(10) Patent No.: US 9,809,825 B2
(45) Date of Patent: Nov. 7, 2017

(54) METHOD FOR PRODUCING ARCHAEAL PROTEIN

(71) Applicant: National Institute of Advanced Industrial Science and Technology, Tokyo (JP)

(72) Inventors: Kazuhiko Ishikawa, Osaka (JP); Seiichirou Kishishita, Hiroshima (JP); Tatsuya Fujii, Hiroshima (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 15/288,203

(22) Filed: Oct. 7, 2016

(65) Prior Publication Data

US 2017/0159062 A1 Jun. 8, 2017

Related U.S. Application Data

(63) Continuation-in-part of application No. PCT/JP2015/061068, filed on Apr. 9, 2015.

(30) Foreign Application Priority Data

Apr. 10, 2014 (JP) ................. 2014-081115

(51) Int. Cl.
*C12N 9/24* (2006.01)
*C12N 15/80* (2006.01)
*C12N 9/42* (2006.01)

(52) U.S. Cl.
CPC .......... *C12N 15/80* (2013.01); *C12N 9/2437* (2013.01); *C12Y 302/01004* (2013.01)

(58) Field of Classification Search
CPC ................ C12Y 302/01; C12N 9/24
See application file for complete search history.

(56) References Cited

FOREIGN PATENT DOCUMENTS

| JP | 2007174962 | 7/2007 |
| JP | 2008271927 | 11/2008 |
| WO | WO 2008/139641 | 11/2008 |
| WO | WO 2014/192647 | 12/2014 |

OTHER PUBLICATIONS

Ando, et al., "Hyperthermostable Endoglucanase from *Pyrococcus horikoshii*" Applied and Environmental Microbiology Jan. 2002, p. 430-433.
Bauer, et al., "An Endoglucanase, EgIA, from the Hyperthermophilic Archaeon *Pyrococcus furious* Hydrolyzes β-1,4 Bonds in Mixed-Linkage (1→3),(1→4)-β-D-Glucans and Cellulose", Journal of Bacteriology, Jan. 1999, pp. 284-290.
Fujii, et al., "Draft Genome Sequence of *Talaromyces cellulolyticus* Strain Y-94, a Source of Lignocellulosic Biomass-Degrading Enzymes", Genome Announcements, vol. 3, Issue 1, 2015.
Inoue, et al., "Constructions of a starch-inducible homologous expression system to produce cellulolytic enzymes from *Acremonium cellulolyticus*", J. Ind. Microbiol Biotechnol (2013) 40:823-830.
Kishishita, et al., "Heterologous expression of hyperthermophilic cellulases of archaea *Pyrococcus* sp. By fungus *Talaromyces cellulolyticus*",J. Ind. Microbiol Biotechnol (2015) 42:137-141.
Shida, et al., "Expression of the Extremely Thermostable Archaeal β-Glucosidase in the Filamentous Fungus *Trichoderma reesei*", Abstracts of the Annual Meeting of the Society for Biotechnology, Japan, Aug. 25, 2013, p. 64, 1 P-187.

*Primary Examiner* — Maryam Monshipouri
(74) *Attorney, Agent, or Firm* — Cesari and McKenna, LLP

(57) ABSTRACT

An object of the present invention is to provide a means for producing an archaeal protein by extracellular secretion. The system for secretory production of an archaeal protein uses a fungus belonging to the genus *Talaromyces* as a host.

16 Claims, 2 Drawing Sheets

SEQUENCE LISTING

<160> NUMBER OF SEQ ID NOS: 7

<210> SEQ ID NO 1
<211> LENGTH: 458
<212> TYPE: PRT
<213> ORGANISM: Pyrococcus horikoshii

<400> SEQUENCE: 1

```
Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Glu Thr Pro Ile His Leu Phe
50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
        115                 120                 125

Gly Leu Asp Ser Leu Gln Ile Met Glu Lys Ile Ile Lys Lys Ala Gly
    130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
        195                 200                 205

Pro Ala Ala Tyr Thr Asp Gly Thr Gly Ala Thr Trp Gly Met Gly Asn
    210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
                245                 250                 255

Thr Asn Pro Lys Thr Asp Ser Ser Tyr Lys Trp Gly Tyr Asn Ala Trp
            260                 265                 270

Trp Gly Gly Asn Leu Met Ala Val Lys Asp Tyr Pro Val Asn Leu Pro
        275                 280                 285

Arg Asn Lys Leu Val Tyr Ser Pro His Val Tyr Gly Pro Asp Val Tyr
    290                 295                 300

Asn Gln Pro Tyr Phe Gly Pro Ala Lys Gly Phe Pro Asp Asn Leu Pro
305                 310                 315                 320
```

```
Asp Ile Trp Tyr His His Phe Gly Tyr Val Lys Leu Glu Leu Gly Tyr
            325                 330                 335

Ser Val Val Ile Gly Glu Phe Gly Lys Tyr Gly His Gly Gly Asp
        340                 345                 350

Pro Arg Asp Val Ile Trp Gln Asn Lys Leu Val Asp Trp Met Ile Glu
            355                 360                 365

Asn Lys Phe Cys Asp Phe Phe Tyr Trp Ser Trp Asn Pro Asp Ser Gly
        370                 375                 380

Asp Thr Gly Gly Ile Leu Gln Asp Asp Trp Thr Ile Trp Glu Asp
385                 390                 395                 400

Lys Tyr Asn Asn Leu Lys Arg Leu Met Asp Ser Cys Ser Lys Ser Ser
            405                 410                 415

Ser Ser Thr Gln Ser Val Ile Arg Ser Thr Thr Pro Thr Lys Ser Asn
            420                 425                 430

Thr Ser Lys Lys Ile Cys Gly Pro Ala Ile Leu Ile Ile Leu Ala Val
            435                 440                 445

Phe Ser Leu Leu Leu Arg Arg Ala Pro Arg
        450                 455

<210> SEQ ID NO 2
<211> LENGTH: 1377
<212> TYPE: DNA
<213> ORGANISM: Pyrococcus horikoshii

<400> SEQUENCE: 2
atggagggga atactattct aaaatcgta  ctaatttgca ctattttagc aggcctattc      60
gggcaagtcg tgccagtata tgcagaaaat acaacatatc aaacaccgac tggaatttac    120
tacgaagtga gaggagatac gatatacatg attaatgtca ccagtggaga ggaaactccc    180
attcatctct ttggtgtaaa ctggtttggc tttgaaacac taatcatgt  agtgcacgga    240 ctttggaaga gaaactggga agacatgctt cttcagatca aaagcttagg cttcaatgca    300
ataagacttc ctttctgtac tgagtctgta aaaccaggaa cacaaccaat tggaatagat    360
tacagtaaaa atccagatct tcgtggacta gatagcctac agattatgga aaagatcata    420
aagaaggccg agatcttgg  tatctttgtc ttactcgact atcataggat aggatgcact    480
cacatagaac ccctctggta cacggaagac ttctcagagg aagactttat taacacatgg    540
atagaggttg ccaaaaggtt cggtaagtac tggaacgtaa taggggctga tctaaagaat    600
gagcctcata gtgttacctc accccagct  gcttatacag atggtaccgg gctacatgg     660 ggtatgggaa acctgcaac  cgattggaac ttggcggctg agaggatagg aaaagcgatt    720
ctgaaggttg cccctcattg gttgatattc gtggagggga cacaatttac taatccgaag    780
actgacagta gttacaaatg gggctacaac gcttggtggg gaggaaatct aatggccgta    840
aaggattatc cagttaactt acctaggaat aagctagtat acagccctca cgtatatggg    900
ccagatgtct ataatcaacc gtactttggt cccgctaagg ttttccgga  taatcttcca    960 gatatctggt atcaccactt tggatacgta aaattagaac taggatattc agttgtaata   1020
ggagagtttg gaggaaaata tgggcatgga ggcgatccaa gggatgttat atggcaaaat   1080
aagctagtta ttggatgat  agagaataaa ttttgtgatt tcttttactg gagctggaat   1140
ccagatagtg gagataccgg aggattccta caggatgatt ggacaacaat atgggaagat   1200
aagtataata acctgaagag attgatggat agttgttcca aaagttcttc aagtactcaa   1260
tccgttattc ggagtaccac ccctacaaag tcaaatacaa gtaagaagat tgtgggacca   1320
```
gcaattctta tcatcctagc agtattctct cttctcttaa gaagggctcc caggtag    1377

<210> SEQ ID NO 3
<211> LENGTH: 319
<212> TYPE: PRT
<213> ORGANISM: Pyrococcus furiosus

<400> SEQUENCE: 3

```
Met Ser Lys Lys Phe Val Ile Val Ser Ile Leu Thr Ile Leu Leu
1               5                   10                  15

Val Gln Ala Ile Tyr Phe Val Glu Lys Tyr His Thr Ser Glu Asp Lys
            20                  25                  30

Ser Thr Ser Asn Thr Ser Ser Thr Pro Pro Gln Thr Thr Leu Ser Thr
        35                  40                  45

Thr Lys Val Leu Lys Ile Arg Tyr Pro Asp Asp Gly Glu Trp Pro Gly
    50                  55                  60

Ala Pro Ile Asp Lys Asp Gly Asp Gly Asn Pro Glu Phe Tyr Ile Glu
65                  70                  75                  80

Ile Asn Leu Trp Asn Ile Leu Asn Ala Thr Gly Phe Ala Glu Met Thr
                85                  90                  95

Tyr Asn Leu Thr Ser Gly Val Leu His Tyr Val Gln Gln Leu Asp Asn
            100                 105                 110

Ile Val Leu Arg Asp Arg Ser Asn Trp Val His Gly Tyr Pro Glu Ile
        115                 120                 125

Phe Tyr Gly Asn Lys Pro Trp Asn Ala Asn Tyr Ala Thr Asp Gly Pro
    130                 135                 140

Ile Pro Leu Pro Ser Lys Val Ser Asn Leu Thr Asp Phe Tyr Leu Thr
145                 150                 155                 160

Ile Ser Tyr Lys Leu Glu Pro Lys Asn Gly Leu Pro Ile Asn Phe Ala
                165                 170                 175

Ile Glu Ser Trp Leu Thr Arg Glu Ala Trp Arg Thr Thr Gly Ile Asn
            180                 185                 190

Ser Asp Glu Gln Glu Val Met Ile Trp Ile Tyr Tyr Asp Gly Leu Gln
        195                 200                 205

Pro Ala Gly Ser Lys Val Lys Glu Ile Val Pro Ile Ile Val Asn
    210                 215                 220

Gly Thr Pro Val Asn Ala Thr Phe Glu Val Trp Lys Ala Asn Ile Gly
225                 230                 235                 240

Trp Glu Tyr Val Ala Phe Arg Ile Lys Thr Pro Ile Lys Glu Gly Thr
                245                 250                 255

Val Thr Ile Pro Tyr Gly Ala Phe Ile Ser Val Ala Ala Asn Ile Ser
            260                 265                 270

Ser Leu Pro Asn Tyr Thr Glu Leu Tyr Leu Glu Asp Val Glu Ile Gly
        275                 280                 285

Thr Glu Phe Gly Thr Pro Ser Thr Thr Ser Ala His Leu Glu Trp Trp
    290                 295                 300

Ile Thr Asn Ile Thr Leu Thr Pro Leu Asp Arg Pro Leu Ile Ser
305                 310                 315
```

<210> SEQ ID NO 4
<211> LENGTH: 960
<212> TYPE: DNA
<213> ORGANISM: Pyrococcus furiosus

<400> SEQUENCE: 4
atgagcaaga aaaagttcgt catcgtatct atcttaacaa tccttttagt acaggcaata    60

```
tattttgtag aaaagtatca tacctctgag gacaagtcaa cttcaaatac ctcatctaca    120
ccaccccaaa caacactttc cactaccaag gttctcaaga ttagataccc tgatgacggt    180
gagtggccag gagctcctat tgataaggat ggtgatggga acccagaatt ctacattgaa    240
ataaacctat ggaacattct taatgctact ggatttgctg agatgacgta caatttaacc    300
agcggcgtcc ttcactacgt ccaacaactt gacaacattg tcttgaggga tagaagtaat    360
tgggtgcatg gataccccga aatattctat ggaaacaagc catggaatgc aaactacgca    420
actgatggcc aataccatt acccagtaaa gtttcaaacc taacagactt ctatctaaca     480
atctcctata aacttgagcc caagaacgga ctgccaatta acttcgcaat agaatcctgg    540
ttaacgagag aagcttggag aacaacagga attaacagcg atgagcaaga agtaatgata    600
tggatttact atgacggatt acaaccggct ggctccaaag ttaaggagat tgtagtccca    660
ataatagtta acggaacacc agtaaatgct acatttgaag tatggaaggc aaacattggt    720
tgggagtatg ttgcatttag aataaagacc ccaatcaaag agggaacagt gacaattcca    780
tacggagcat ttataagtgt tgcagccaac atttcaagct taccaaatta cacagaactt    840
tacttagagg acgtggagat tggaactgag tttggaacgc caagcactac ctccgcccac    900
ctagagtggt ggatcacaaa cataacacta actcctctag atagacctct tatttcctaa    960
```

<210> SEQ ID NO 5
<211> LENGTH: 72
<212> TYPE: DNA
<213> ORGANISM: Talaromyces cellulolyticus

<400> SEQUENCE: 5

```
atgtctgctc tcaactcttt caacatgtac aagtctgctc tcatcctcgg ctctctcctc     60
gctaccgctg gc                                                         72
```

<210> SEQ ID NO 6
<211> LENGTH: 1167
<212> TYPE: DNA
<213> ORGANISM: Pyrococcus horikoshii

<400> SEQUENCE: 6

```
gaaaacacca cctaccaaac ccctaccggc atctactacg aagtccgagg cgataccatc     60
tacatgatca acgtcacctc tggcgaagaa accctatcc atctcttcgg cgtcaactgg     120
ttcggcttcg aaacccctaa ccatgtcgtc catggcctct ggaagcgaaa ctgggaagat    180
atgctcctcc aaatcaagtc tctcggcttc aacgctatcc gactcccttt ctgcaccgaa    240
tctgtcaagc ctggcacccca acctatcggc atcgattact ctaagaaccc tgatctccga    300
ggcctcgatt ctctccaaat catggaaaag atcatcaaga aggctggcga tctcggcatc    360
ttcgtcctcc tcgattacca tcgaatcggc tgcacccata tcgaacctct ctggtacacc    420
gaagatttct ctgaagaaga tttcatcaac acctggatcg aagtcgctaa gcgattcggc    480
aagtactgga acgtcatcgg cgctgatctc aagaacgaac ctcattctgt cacctctcct    540
cctgctgctt acaccgatgg caccggcgct acctggggca tgggcaaccc tgctaccgat    600
tggaacctcg ctgctgaacg aatcggcaag gctatcctca aggtcgctcc tcattggctc    660
atcttcgtcg aaggcacccca attcaccaac cctaagaccg attcttctta caagtggggc    720
tacaacgctt ggtggggcgg caaccctcatg gctgtcaagg attaccctgt caacctccct    780
cgaaacaagc tcgtctactc tcctcatgtc tacggccctg atgtctacaa ccaaccttac    840
```

-continued

```
ttcggccctg ctaagggctt ccctgataac ctccctgata tttggtacca tcatttcggc    900
tacgtcaagc tcgaactcgg ctactctgtc gtcatcggcg aattcggcgg caagtacggc    960
catggcggcg atcctcgaga tgtcatctgg caaaacaagc tcgtcgattg gatgatcgaa   1020
aacaagttct gcgatttctt ctactggtct tggaaccctg attctggcga taccggcggc   1080
atcctccaag atgattggac caccatctgg gaagataagt acaacaacct caagcgactc   1140
atggattctt gctctaagtc ttcttga                                       1167
```

<210> SEQ ID NO 7
<211> LENGTH: 813
<212> TYPE: DNA
<213> ORGANISM: Pyrococcus furiosus

<400> SEQUENCE: 7

```
aaggtcctca agatccgata ccctgatgat ggcgaatggc ctggcgctcc tatcgataag     60
gatggcgatg gcaaccctga attctacatc gaaatcaacc tctggaacat cctcaacgct    120
accggcttcg ctgaaatgac ctacaacctc acctctggcg tcctccatta cgtccaacaa    180
ctcgataaca tcgtcctccg agatcgatct aactgggtcc atggctaccc tgaaatcttc    240
tacggcaaca agccttggaa cgctaactac gctaccgatg gccctatccc tctcccttct    300
aaggtctcta acctcaccga tttctacctc accatctctt acaagctcga acctaagaac    360
ggcctcccta tcaacttcgc tatcgaatct tggctcaccc gagaagcttg gcgaaccacc    420
ggcatcaact ctgatgaaca agaagtcatg atctggatct actacgatgg cctccaacct    480
gctggctcta aggtcaagga aatcgtcgtc cctatcatcg tcaacggcac ccctgtcaac    540
gctaccttcg aagtctggaa ggctaacatc ggctgggaat acgtcgcttt ccgaatcaag    600
acccctatca aggaaggcac cgtcaccatc ccttacggcg ctttcatctc tgtcgctgct    660
aacatctctt ctctccctaa ctacaccgaa ctctacctcg aagatgtcga aatcggcacc    720
gaattcggca ccccttctac cacctctgct catctcgaat ggtggatcac caacatcacc    780 ctcaccccctc tcgatcgacc tctcatctct tga                               813
```

METHOD FOR PRODUCING ARCHAEAL PROTEIN

CROSS-REFERENCE TO RELATED APPLICATIONS

This application is a continuation-in-part of International Application No. PCT/JP2015/061068, filed on Apr. 9, 2015, which claims priority to Japanese Application No. 2014-081115, filed on Apr. 10, 2014. The contents of both applications are hereby incorporated by reference in their entirety.

BACKGROUND

Technical Field

The invention disclosed herein partly relates to a system for secretory production of archaeal proteins.

Background Art

Archaea are known to produce various useful proteins. For example, thermostable cellulases, which are useful for saccharification of biomass, have been identified from thermophilic archaea or hyperthermophilic archaea (i.e., *Pyrococcus furiosus, Pyrococcus horikoshii, Thermotoga maritima, Sulfolobus shibatae*, and *Sulfolobus solfataricus*).

As a means for industrially producing archaeal proteins, for example, a method for producing hyperthermostable endo-cellulases of *Pyrococcus horikoshii* in *Escherichia coli* has been reported (Non-patent literature (NPL) 1). A method for producing hyperthermostable endo-cellulases of *Pyrococcus furiosus* using *Escherichia coli* as a host has also been reported (Non-patent Literature (NPL) 2).

CITATION LIST

Patent Literature

PTL 1: JP2008-271927

Non-Patent Literature

NPL 1: Ando et al., Appl. Environ. Microbiol., 68, 1, 430-433, 2002
NPL 2: Bauer et al., J. Bacteriol., 181, 1, 284-290

SUMMARY OF INVENTION

Technical Problem

However, previously reported methods could still be further improved. For example, the methods disclosed in NPL 1 and NPL 2 require cellular disruption to obtain a protein since these methods are substantially not capable of producing archaeal proteins by extracellular secretion. In view of this, an object of the present invention is to provide a means for producing archaeal proteins by extracellular secretion.

Solution to Problem

There has been no report regarding the expression of archaeal proteins by secretion even when *Trichoderma reesei*, which is a typical filamentous fungus for high amounts of protein production by expression, is used as a host. Regarding archaeal beta-glucosidase, there is a single report stating that the protein is produced by expression using *Trichoderma reesei* as a host; however, secretion could not be achieved. In view of this, the present inventors conducted extensive research to solve the above problems, and found that the use of filamentous fungi of the genus *Talaromyces* as a host enables the production by secretion. The present invention has been accomplished as a result of further research and improvements based on these findings.

Representative examples of the present invention are described below.

Item 1.

A system for secretory production of an archaeal protein, the system using a fungus belonging to the genus *Talaromyces* as a host.

Item 2.

The system according to Item 1, wherein the fungus belonging to the genus *Talaromyces* is transformed with an expression vector comprising:

a promoter region that functions in the fungus belonging to the genus *Talaromyces*, a secretion signal region located downstream of the promoter region, an archaeal protein-coding region located downstream of the secretion signal region, and a terminator region located downstream of the archaeal protein-coding region.

Item 3.

The system according to Item 2, wherein the secretion signal region has the base sequence of SEQ ID NO: 5.

Item 4.

The system according to Item 2 or 3, wherein both the promoter region and the terminator region are of glucoamylase from *Talaromyces cellulolyticus*.

Item 5.

The system according to any one of Items 2 to 4, wherein the codon usage in the archaeal protein-coding region is optimized for expression in a fungus belonging to the genus *Talaromyces*.

Item 6.

The system according to any one of Items 1 to 5, wherein the archaeal protein is a cellulase from the genus *Pyrococcus*.

Item 7.

The system according to any one of Items 2 to 6, wherein the archaeal protein-coding region has the base sequence of SEQ ID NO: 6 or 7.

Item 8.

A method for producing an archaeal protein by secretion using the system of any one of Items 1 to 7.

Item 9.

The method according to Item 8, wherein the method comprises a step of culturing a fungus belonging to the genus *Talaromyces*.

Item 10.

Use of a fungus belonging to the genus *Talaromyces* in the secretory production of an archaeal protein.

Advantageous Effects of Invention

The present invention enables efficient secretory production of archaeal proteins. Thus, the present invention makes it possible to industrially and stably provide archaeal proteins. According to the present invention, an archaeal protein can be obtained without crushing a microorganism that produces the protein.

DESCRIPTION OF EMBODIMENTS

Figure 1:
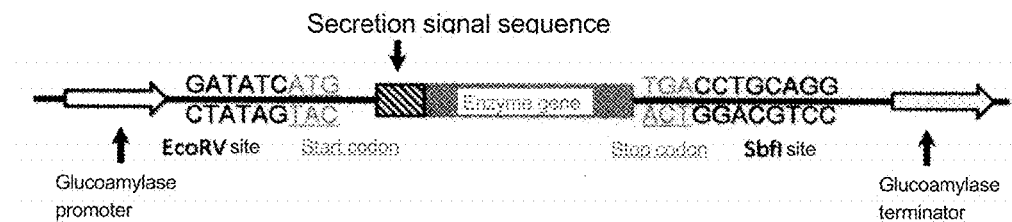
FIG. 1 shows the structure of a vector constructed in the Examples.

In secretory production of archaeal proteins, it is preferable to use fungi belonging to the genus *Talaromyces* as a host. The fungi belonging to the genus *Talaromyces* as used herein are a species of filamentous fungi and are used in the industry to produce antibiotics and various enzymes. The fungi belonging to the genus *Talaromyces* are not particularly limited as long as secretory production of archaeal proteins is possible; it is preferable to use fungi that themselves have an ability to produce proteins (preferably cellulases) by secretion. Examples of such fungi belonging to the genus *Talaromyces* include *Talaromyces cellulolyticus*, *Talaromyces flavus*, *Talaromyces marneffei*, *Talaromyces pinophilus*, *Talaromyces emersonii*, *Talaromyces stipitatus*, and the like. As *Talaromyces cellulolyticus*, it is preferable to use Y-94, YP-4, TN, C-1, and CF-2612 strains. Until recently, *Talaromyces cellulolyticus* had been categorized as *Acremonium cellulolyticus*.

The archaeal protein produced by secretion using fungi belonging to the genus *Talaromyces* as a host may be any archaeal protein and may be appropriately selected according to the purpose. Examples of archaeal proteins include industrially used various enzymes (e.g., hydrolase, oxidoreductase, transferase, isomerase, synthetase, ligase, and lyase). More specific examples include cellulase, xylanase, amylase, lipase, protease, xylanase, pectinase, chitinase, kinase, luciferase, and the like. In one embodiment, a preferable enzyme is a cellulase, such as endo-cellulase, exo-cellulase (cellobiohydrolase), and β-glucosidase. In one embodiment, it is preferable that the cellulase is a monomeric protein. It is also preferable that the cellulase belongs to glycosyl hydrolase family 5 or 12 because most of the cellulases in these families are monomeric cellulases.

In one embodiment, a protein produced by secretion is preferably an endo-cellulase. An endo-cellulase refers to an enzyme that catalyzes a reaction for hydrolysis of β-glycosidic linkages in amorphous cellulose molecules. The activity thereof can be evaluated mainly using carboxymethyl cellulose (CMC) as a substrate. For example, the activity is determined in the following manner: 50 μL of an enzyme dilution is added to 950 μL of 50 mM acetic acid buffer containing 1% CMC; then, after 30 minutes, the reaction is stopped by adding 3 mL of a strong alkaline DNS assay solution, and the amount of reducing ends released from CMC is quantified by the DNS method. One U is defined as the activity in which 1 μmol of reducing sugars are generated per minute.

The type of archaea, which is the origin of the proteins produced by secretion, may be any archaea and may be suitably selected according to the type of proteins to be produced. In one embodiment, it is preferable to use archaea classified into, for example, hyperthermophilic, halophilic, or acidophilic archaea. Preferable examples of hyperthermophilic archaea include archaea belonging to the genera *Pyrococcus*, *Thermococcus*, *Thermotoga*, and *Sulfolobus*. More specific examples include *Pyrococcus horikoshii*, *Pyrococcus furiosus*, *Thermococcus kodakaraensis*, *Thermotoga maritima*, *Sulfolobus shibatae*, and *Sulfolobus solfataricus*.

In one embodiment, proteins produced by secretion are preferably thermostable endo-cellulases from the genus *Pyrococcus*. More specifically, a thermostable endo-cellulase from *Pyrococcus horikoshii* and a thermostable endo-cellulase from *Pyrococcus furiosus* are preferable. The amino acid sequence of the thermostable endo-cellulase from *Pyrococcus horikoshii* and a base sequence encoding this amino acid sequence are respectively shown in SEQ ID NOs: 1 and 2. The amino acid sequence of the thermostable endo-cellulase from *Pyrococcus furiosus* and a base sequence encoding this amino acid sequence are respectively shown in SEQ ID NOs: 3 and 4. The thermostable endo-cellulase from *Pyrococcus furiosus* and thermostable endo-cellulase from *Pyrococcus horikoshii* are stable even in the temperature range of 80° C. or higher, and show high activity. Their use (in particular in saccharification of biomass) is thus promising.

Archaeal proteins may be found in nature or may be artificially modified. For example, it is possible to use a protein having an amino acid sequence with 80% or more, 85% or more, 90% or more, 95% or more, or 98% or more identity to an amino acid sequence of known proteins (e.g., the amino acid sequence shown in SEQ ID NO: 1 or 3), and having endo-cellulase activity.

In the amino acid sequence of SEQ ID NO: 1, the amino acid region from position 1 to position 28 is a signal sequence, the amino acid region from position 29 to position 416 is an active domain, and the region after position 417 is a functionally unknown membrane-binding region. In the amino acid sequence of SEQ ID NO: 3, the amino acid region from position 1 to position 18 is a signal sequence, the amino acid region from position 19 to position 49 is a functionally unknown region, and the region after position 50 is an active domain.

It is preferable that the fungi belonging to the genus *Talaromyces* for the secretory production of archaeal proteins is transformed with a vector incorporating an archaeal protein-encoding base sequence in a manner that allows for the expression. Such a vector preferably comprises a promoter region, a secretion signal region located downstream of the promoter region, an archaeal protein-coding region located downstream of the secretion signal region, and a terminator region located downstream of the archaeal protein-coding region, all of which regions function in fungi belonging to the genus *Talaromyces*.

The promoter region and terminator region that function in fungi belonging to the genus *Talaromyces* are not particularly limited, and may be suitably modified and selected. For example, they may be suitably selected from promoter and terminator regions of filamentous fungi, and preferably selected from promoter and terminator regions of the genus *Talaromyces*. A plurality of promoter and terminator regions from the genus *Talaromyces* have already been known. Further, novel promoter and terminator regions are easily searchable based on well-known promoter and terminator base sequences, or well-known protein sequences, using known techniques. The origin of the promoter and terminator regions may be fungi belonging to the genus *Talaromyces* to be used as a host, or may be other fungi. Examples of suitable promoters and terminators from fungi belonging to the genus *Talaromyces* include starch-inducible glucoamylase promoter and glucoamylase terminator, which are used in the Examples described below. Additionally, promoters and terminators that control the expression of Cellobiohydrolase I present in a fungus belonging to the genus *Talaromyces* are also suitably used. They can more strongly express genes by adjusting culture conditions.

The secretion signal region is not particularly limited as long as it allows archaeal proteins to be extracellularly secreted from fungi belonging to the genus *Talaromyces*, and any modification and selection can be made. For example, it is possible to use signal regions of archaea. The origin of the signal region may be the same or different from that of proteins to be produced by secretion; the signal region may be one naturally present in the proteins to be produced by secretion. Specific examples of preferred signal regions include the region encoding a secretion signal peptide of Cellobiohydrolase from *Talaromyces cellulolyticus* shown in SEQ ID NO: 5.

The regions (or base sequences) encoding a secretion signal and an archaeal protein are not particularly limited as long as the expression in a fungus belonging to the genus *Talaromyces* is possible. It is preferable that the codon usage is optimized for suitable expression in a fungus belonging to the genus *Talaromyces*. The codon usage may be optimized with respect to a part or all the minor codons in the base sequences encoding proteins; however, it is preferable that as many minor codons as possible are optimized. The term "minor codon" as used herein refers to codons other than most frequently used codons (major codons) among those coding for specific amino acids in a fungus belonging to the genus *Talaromyces*. Optimization of codon usage is desirably performed to such an extent that the optimization does not change the amino acids encoded by the codons. The technique for codon usage optimization is known, and any means may be used. For example, optimization may be performed by introducing mutations using a nucleic acid primer or by nucleic acid synthesis.

The optimization of the codon usage to increase the amount of expression in a fungus belonging to the genus *Talaromyces* may be performed by changing codons encoding each amino acid to the following: phenylalanine (UUC), leucine (CUC), isoleucine (AUC), valine (GUC), serine (UCU), proline (CCU), threonine (ACC), alanine (GCU), tyrosine (UAC), histidine (CAU), glutamine (CAA), asparagine (AAC), lysine (AAG), aspartic acid (GAU), glutamic acid (GAA), cysteine (UGC), arginine (CGA), and glycine (GGC). SEQ ID NO: 6 shows the base sequence encoding thermostable endo-cellulase from *Pyrococcus horikoshii*, the codon usage of which sequence has been optimized for the expression in the genus *Talaromyces*. SEQ ID NO: 8 shows the base sequence encoding thermostable endo-cellulase from *Pyrococcus furiosus*, the codon usage of which sequence has been optimized for the expression in the genus *Talaromyces*.

The expression vector containing a promoter region, a secretion signal region, a protein-coding region, and a terminator region in a manner that allows for protein expression may be linked via an appropriate restriction enzyme recognition site. The expression vector may also contain a selectable marker gene, such as a drug resistance gene and an auxotrophic complementary gene. Such an expression vector may be constructed by using known methods.

Known methods may be used to introduce an expression vector into a fungus belonging to the genus *Talaromyces* used as a host. For example, an electroporation method, a polyethylene glycol method, an *Agrobacterium* method, or the like may be used. The vector to be introduced may be a single vector, or two or more types of vectors. The recombination of the gene of a fungus of the genus *Talaromyces* using the introduced gene may be performed by homologous recombination or non-homologous recombination. To achieve an increased amount of expression by making use of homologous recombination, it is preferable to perform homologous recombination at the site of cellulase gene of a fungus belonging to the genus *Talaromyces*. In particular, homologous recombination at the site of cellobiohydrolase gene of a fungus belonging to the genus *Talaromyces* is preferable to achieve a high amount of enzyme expression. Further, in homologous recombination at the site of endo-cellulase gene of a fungus belonging to the genus *Talaromyces*, the cellobiohydrolase activity is not decreased, and the biomass decomposition activity is thus less likely to be reduced, compared with homologous recombination at the site of a cellobiohydrolase gene; thus, homologous recombination at the site of endo-cellulase gene of a fungus belonging to the genus *Talaromyces* is preferable. In all of these cases, homologous recombination is preferably performed at a site that is linked to a promoter, signal peptide, terminator, and the like, of target cellobiohydrolase and/or endoglucanase genes so that the promoter and terminator of endogenous cellobiohydrolase gene and/or endo-cellulase gene of a fungus belonging to the genus *Talaromyces* are used as is.

For non-homologous recombination, the recombination target genes are not particularly limited. In non-homologous recombination, the loss of cellulase gene rarely occurs, and the biomass decomposition activity is thus less likely to be reduced; therefore, non-homologous recombination is preferable. When non-homologous recombination is performed, a gene to which a promoter and a terminator are suitably linked is used to express a target protein.

When the thus transformed host is cultured, a target archaeal protein is expressed and extracellularly secreted. Culture of a transformant is performed in accordance with known methods. As a medium, for example, commonly used components may be used. For example, a carbon source may be used, such as glucose, sucrose, cellulose, sugar syrup, dextrin, starch, glycerol, molasses, and animal and plant oils. Further, a nitrogen source may be used, such as polypeptone, soybean flour, wheat germ, cotton seed meal, bouillon, peptone, yeast extract, ammonium sulfate, potassium nitrate, and urea. Additionally, it is also effective to add, as required, inorganic salts, such as potassium chloride, magnesium sulfate, monopotassium phosphate, zinc sulfate, manganese sulfate, and copper sulfate, that can generate ions of sodium, potassium, calcium, magnesium, cobalt, chlorine, phosphate, and sulfate, as well as other ions. It is also possible to add micronutrients, such as various vitamins, amino acids, and nucleotides, as well as selection drugs, such as antibiotics, as required. In addition, it is possible to suitably add organic substances and inorganic substances that help cell growth and accelerate the expression of introduced genes. Examples of such substances include cellulose, xylan, lactose, and the like.

The culture method may be arbitrarily selected, and various culture systems, such as shaking culture, spinner culture, agitation culture, stationary culture, and continuous culture, may be used, with shaking culture or spinner culture being preferable. The culture temperature is usually 20 to 35° C., and preferably 25 to 31° C. The culture time may be suitably set according to the amount of target protein to be produced by secretion, and is, for example, 3 to 10 days, and preferably 4 to 9 days.

The target protein secreted in the culture medium by culturing the host may be used as is as the culture medium. It is also possible to concentrate, extract, and/or purify the culture medium to obtain a concentrate, an extract, a roughly purified protein, or a purified protein. Any techniques may be used for concentration, extraction, and purification. For example, techniques such as filtration, centrifugation, salting-out, solvent precipitation, dialysis, ultrafiltration, gel electrophoresis, and various chromatographies (e.g., ion exchange, hydrophobic, reverse phase, gel filtration, affinity) may be used in combination.

EXAMPLES

The present invention is described in more detail with reference to Examples but is not limited to these.

1. Preparation of Recombinant Vector

A polynucleotide (hereinafter sometimes also referred to as "sequence H") having a base sequence in which the base sequence (SEQ ID NO: 6) encoding a thermostable endo-cellulase from *Pyrococcus horikoshii*, the codons of whose sequence had been modified for the expression in the genus *Talaromyces*, was linked to the downstream of the base sequence (SEQ ID NO: 5) encoding the secretion signal peptide of cellobiohydrolase from *Talaromyces cellulolyticus* was prepared by a synthetic method. Further, a polynucleotide (hereinafter sometimes also referred to as "sequence F") having a base sequence in which the base sequence (SEQ ID NO: 7) encoding a thermostable endo-cellulase from *Pyrococcus furiosus*, the codons of whose sequence had been modified for the expression in the genus *Talaromyces*, was linked to the downstream of the base sequence (SEQ ID NO: 5) encoding the secretion signal peptide of cellobiohydrolase from *Talaromyces cellulolyticus* was prepared by a synthetic method. These two types of polynucleotides were incorporated into plasmid vectors (Inoue et al., J. Ind. Microbiol. Biotechnol., 2013, 40: 823-830) containing starch-inducible glucoamylase promoter and glucoamylase terminator of *Talaromyces cellulolyticus*. In this manner, a plasmid vector having the sequence H between the glucoamylase promoter and glucoamylase terminator (hereinafter sometimes referred to as "the vector H") and a plasmid vector having the sequence F between the glucoamylase promoter and glucoamylase terminator (hereinafter sometimes referred to as "the vector F") were produced (FIG. 1). As shown in FIG. 1, restriction enzyme recognition sites (ECORV site and Sbfl site) were appropriately provided at the linkages between each region.

2. Production of Transformed *Talaromyces*

The recombination vectors prepared in 1. above were separately introduced into *Talaromyces cellulolyticus* YP-4. The introduction was performed by a protoplast PEG method, and the transformants were selected using a medium for uracil-auxotrophic selection. The following is the composition of the medium for uracil-auxotrophic selection:

1 mass % glucose,
1.0 M sucrose,
1.5 mass % agar,
0.04 mass % $KH_2PO_4$ (pH 5.5),
0.01 mass % potassium chloride,
0.01 mass % $MgSO_4.7H_2O$,
0.05 mass % ammonium chloride, and
0.5 mass % trace element.

The trace element was obtained by dissolving 200 mg of $CuSO_4.5H_2O$, 200 mg of $MnCl_2.5H_2O$, and 200 mg of $ZnSO_4.7H_2O$ in distilled water, and filling up to 100 mL. A PCR method was used to confirm the insertion of the target gene into the genomic DNAs of the obtained transformants.

3. Secretory Production of Archaeal Protein Using Transformed *Talaromyces*

Each transformant was separately inoculated into a 100-mL Erlenmeyer flask containing 10 mL of liquid medium, and cultured at 220 rpm for four days at a pH of 4.0 at 28.5° C. The composition of the medium was as follows:

1 mass % corn steep liquor,
2 mass % starch,
0.5 mass % $(NH_4)_2SO_4$,
2.4 mass % $KH_2PO_4$,
0.47 mass % potassium tartrate dihydrate,
0.12 mass % $MgSO_4$,
0.1 mass % Tween 80,
0.2 mass % urea, and
0.1 mass % Trace element.

Each of the obtained culture media was subjected to centrifugal separation at 3500 rpm for 10 minutes, and separated into a culture supernatant and cells. The culture supernatant was subjected to heat treatment at 70° C. for 15 minutes, followed by the measurement of cellulase activity to confirm its presence. The protein amounts of thermostable endo-cellulase from *Pyrococcus horikoshii*, and thermostable endo-cellulase from *Pyrococcus furiosus* contained in the culture supernatants after heat treatment were measured by a BCA method, both of which resulted in the expression amount of 100 mg/L or more, on a BSA basis.

4. Measurement of Molecular Weight

Figure 2:
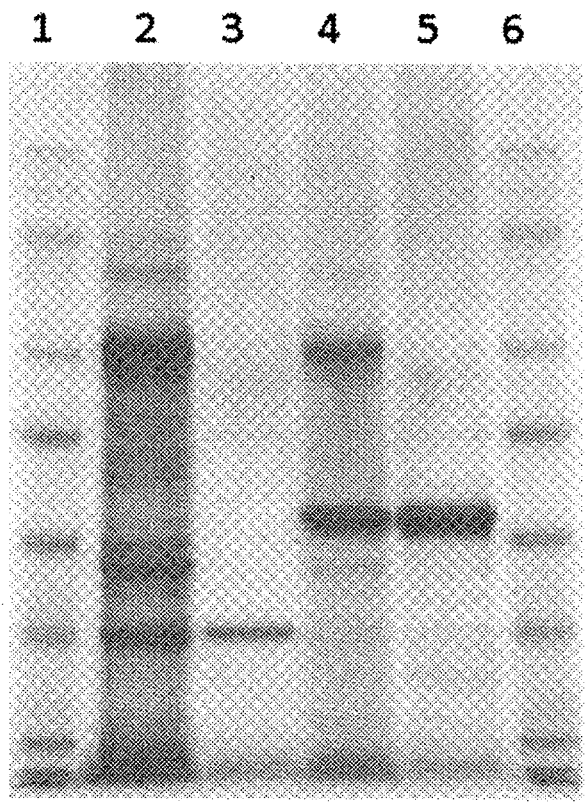
FIG. 2 shows the molecular weight determined by SDS-PAGE analysis of a thermostable endo-cellulase from *Pyrococcus furiosus* and thermostable endo-cellulase from *Pyrococcus horikoshii* recombinantly produced by secretion in the Examples using a fungus of *Talaromyces* as a host. Lanes 1 and 6: molecular markers; Lane 2: a sample obtained from a culture medium in which the thermostable endo-cellulase from *Pyrococcus furiosus* was produced by secretion; Lane 3: a sample obtained by heating a culture medium in which the thermostable endo-cellulase from *Pyrococcus furiosus* was produced by secretion, the heating being performed at 70° C. for 15 minutes to remove contaminating proteins; Lane 4: a sample obtained from a culture medium in which the thermostable endo-cellulase from *Pyrococcus horikoshii* was produced by secretion; and Lane 5: a sample obtained by heating a culture medium in which the thermostable endo-cellulase from *Pyrococcus horikoshii* was produced by secretion, the heating being performed at 70° C. for 15 minutes to remove contaminating proteins.

The culture supernatants obtained in 3. above were subjected to heat-treatment at 70° C. for 15 minutes, and contaminating proteins were removed, followed by the measurement of the molecular weight by SDS-PAGE. The molecular weights of thermostable endo-cellulase from *Pyrococcus horikoshii* and thermostable endo-cellulase from *Pyrococcus furiosus* were 44 kDa and 30 kDa, respectively, and they were thus confirmed to be target enzymes (FIG. 2).

5. Measurement of Thermostable Endo-cellulase Activity

Figure 3:
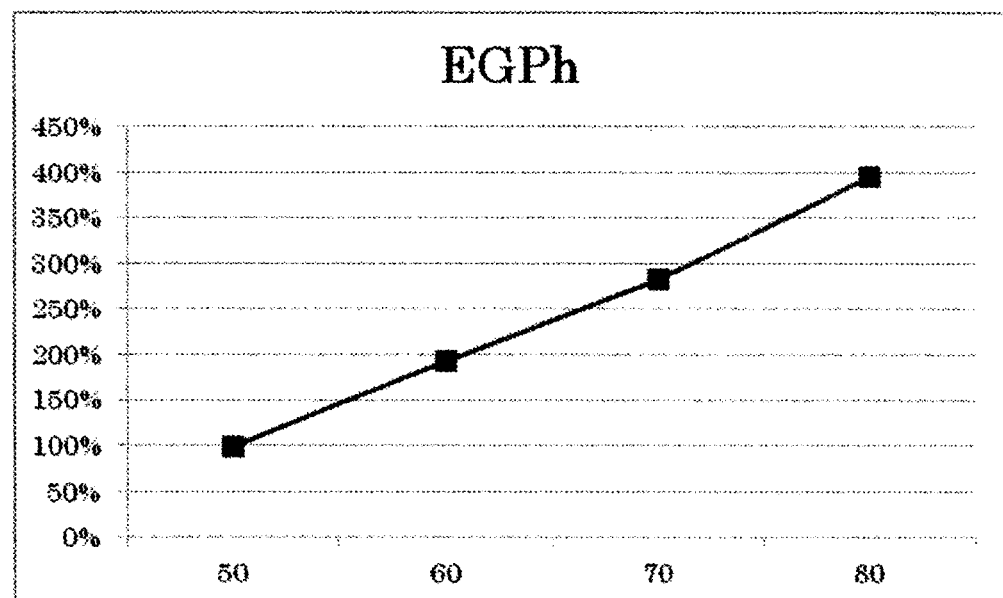
FIG. 3 shows the results of the endoglucanase activity measured at 50° C., 60° C., 70° C., and 80° C., with respect to the thermostable endo-cellulase from *Pyrococcus furiosus* recombinantly produced by secretion using a fungus of the genus *Talaromyces* as a host.
Figure 4:
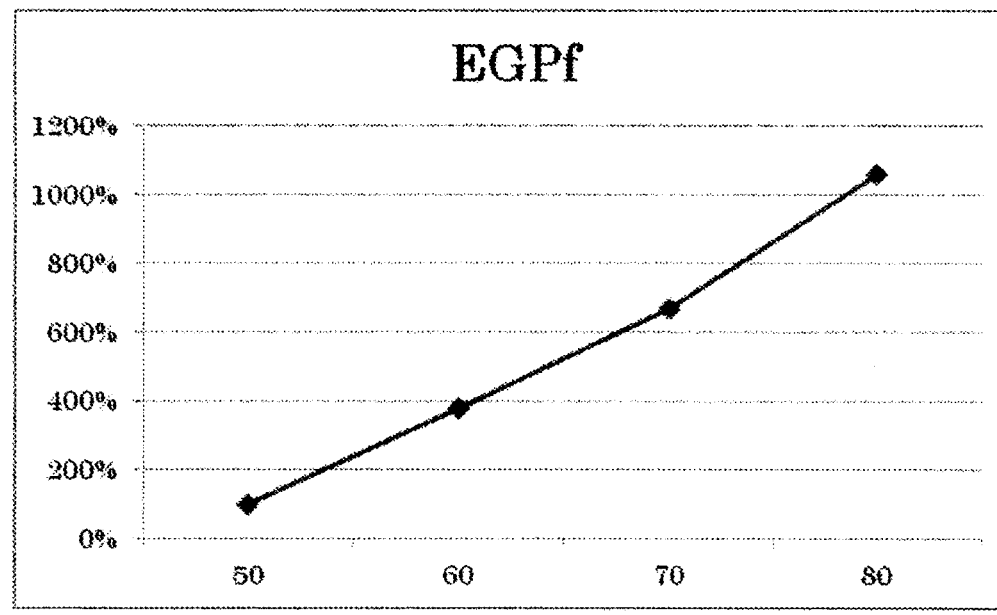
FIG. 4 shows the results of the endoglucanase activity measured at 50° C., 60° C., 70° C., and 80° C., with respect to the thermostable endo-cellulase from *Pyrococcus horikoshii* recombinantly produced by secretion using a fungus of the genus *Talaromyces* as a host.

The thermostable endo-cellulase from *Pyrococcus horikoshii* and thermostable endo-cellulase from *Pyrococcus furiosus* expressed in the filamentous fungi of the genus *Talaromyces* were purified, and the endoglucanase activity was measured at reaction temperatures of 50, 60, 70, and, 80° C. Specifically, 3.0 μg of thermostable endo-cellulase from *Pyrococcus horikoshii* or 1.5 μg of thermostable endocellulase from *Pyrococcus furiosus* was added per 1 mL of 20 mM sodium acetate buffer containing CMC in an amount of 1 mass %, and reacted for 1 hour at each temperature. The amount of generated reducing ends was measured by DNS method to determine the activity. The results confirmed a thermal resistance as high as that of wild-type endoglucanase. These enzymes were thus confirmed to have thermal resistance (FIGS. 3 and 4). In FIGS. 3 and 4, the horizontal axis represents the measurement temperature, while the longitudinal axis represents the activity at each temperature, relative to the activity at 50° C., which is considered to be 100%.

The invention claimed is:

1. A method of producing an archaeal protein, comprising a step of cultivating a fungus belonging to the genus *Talaromyces*,
wherein the fungus has been transformed with an expression vector comprising:
a promoter region that functions in the fungus;
a secretion signal region located downstream of the promoter region, the secretion signal region encoding a secretion signal peptide of a cellobiohydrolase gene from the genus *Talaromyces*;
a coding region for the archaeal protein located downstream of the secretion signal region; and
a terminator region located downstream of the coding region, and
wherein the fungus secretes the archaeal protein.

2. The method according to claim 1, wherein the secretion signal region has the base sequence of SEQ ID NO: 5.

3. The method according to claim 1, wherein both the promoter region and the terminator region are of glucoamylase from *Talaromyces cellulolyticus*.

4. The method according to claim 1, wherein the codon usage in the coding region is optimized for expression in the fungus.

5. The method according to claim 1, wherein the archaeal protein is a cellulase from the genus *Pyrococcus*.

6. The method according to claim 1, wherein the coding region has the base sequence of SEQ ID NO: 6 or 7.

7. The method according to claim 2, wherein both the promoter region and the terminator region are of glucoamylase from *Talaromyces cellulolyticus*.

8. The method according to claim 2, wherein the codon usage in the coding region is optimized for expression in the fungus.

9. The method according to claim 3, wherein the codon usage in the coding region is optimized for expression in the fungus.

10. The method according to claim 2, wherein the archaeal protein is a cellulase from the genus *Pyrococcus*.

11. The method according to claim 3, wherein the archaeal protein is a cellulase from the genus *Pyrococcus*.

12. The method according to claim 4, wherein the archaeal protein is a cellulase from the genus *Pyrococcus*.

13. The method according to claim 2, wherein the coding region has the base sequence of SEQ ID NO: 6 or 7.

14. The method according to claim 3, wherein the coding region has the base sequence of SEQ ID NO: 6 or 7.

15. The method according to claim 4, wherein the coding region has the base sequence of SEQ ID NO: 6 or 7.

16. The method according to claim 5, wherein the coding region has the base sequence of SEQ ID NO: 6 or 7.

* * * * *